US005505731A

United States Patent [19]
Tornier

[11] Patent Number: 5,505,731
[45] Date of Patent: Apr. 9, 1996

[54] SCREW FOR LUMBAR-SACRAL FIXATOR

[75] Inventor: Alain Tornier, Saint-Ismier, France

[73] Assignee: Tornier SA, Saint-Ismier, France

[21] Appl. No.: 295,054

[22] Filed: Aug. 26, 1994

[30] Foreign Application Priority Data

Sep. 1, 1993 [FR] France .................................. 93 10581

[51] Int. Cl.⁶ ........................... A61B 17/70; A61B 17/80; A61B 17/86
[52] U.S. Cl. .................. 606/61; 606/73; 606/69
[58] Field of Search .................. 606/60, 61, 72, 606/73, 69, 70, 71; 411/401, 383, 384, 398; 403/97

[56] References Cited

U.S. PATENT DOCUMENTS

| | | | |
|---|---|---|---|
| 2,696,817 | 12/1954 | Prevo | 606/72 |
| 3,778,610 | 12/1973 | Wolf | 403/97 |
| 4,630,985 | 12/1986 | Simons | 411/386 |
| 4,987,892 | 1/1991 | Krag et al. | 606/61 |
| 5,002,578 | 3/1991 | Loman | 623/23 |
| 5,067,955 | 11/1991 | Cotrel | 606/61 |
| 5,108,395 | 4/1992 | Laurain | 606/73 |
| 5,176,680 | 1/1993 | Vignaud et al. | 606/61 |
| 5,190,543 | 3/1993 | Schläpfer | 606/61 |

Primary Examiner—Stephen C. Pellegrino
Assistant Examiner—Scott B. Markow
Attorney, Agent, or Firm—Dowell & Dowell

[57] ABSTRACT

A screw for a lumbar-sacral fixator for use on the spine wherein the screw comprises a threaded part and a head which has a notched surface which is inclined with respect to an elongated axis of the screw by an angle of approximately 30° to 45°.

11 Claims, 2 Drawing Sheets

SCREW FOR LUMBAR-SACRAL FIXATOR

BACKGROUND OF THE INVENTION

1. Field of the Invention

The present invention relates to a screw for positioning lumbar-sacral fixators which allow a fusion of the vertebral stages damaged during an accident to the spine.

2. History of the Related Art

At the present time, pedicular screws are known, which generally comprise a head provided with a notched surface which lies in a plane parallel to that of the vertical axis of said screw. The head is pierced with a tapped, opening hole which is perpendicular to the axis of the screw. A connecting stem connecting two or more damaged vertebrae comprises at each free end a piece which is pierced with an opening hole. One of the faces of the piece is notched in order to improve contact with that of the pedicular screw. Assembly between the rod and the head of the screw is effected by means of a bolt which is tightened with the aid of a wrench.

It will be noted that tightening of the bolt is effected perpendicularly to the vertical axis of the screw, which considerably complicates assembly. In fact, the free space provided for the passage of the tightening wrench is much reduced.

Moreover, the operator can screw only ⅙ of a turn at once, as the tip of the jaws of the wrench abut against the osseous wall of the transverse processes. In addition, opposite the head of the bolt is located the spine of the vertebra, which prevents the operator from using a screwdriver.

It is a more particular object of the present invention to overcome these drawbacks.

SUMMARY OF THE INVENTION

The pedicular screw according to the invention comprises a threaded part and a semi-spherical head which is provided with a notched surface inclined with respect to the axis of the screw by an angle α of about 30° to 45° with respect to the vertical axis.

The threaded part of the pedicular screw is provided with a conical core of equal resistance comprising sharp threads over the whole length of the threading.

The head of the pedicular screw is provided with a tapped, opening hole which is perpendicular to the notched surface so as to be able to join the connecting stems on the pedicular screws by means of a bolt.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
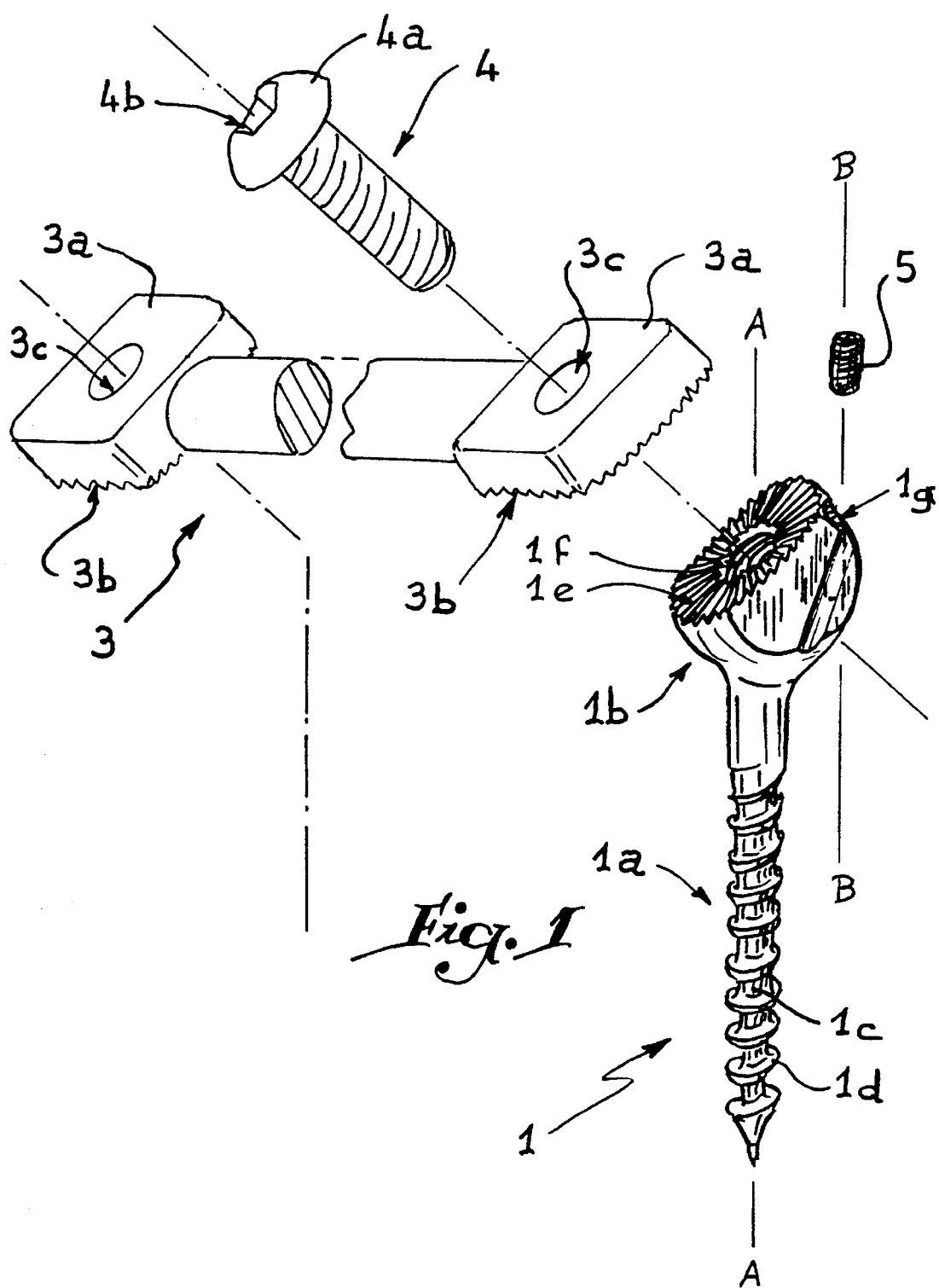
FIG. 1 is an exploded view in perspective illustrating the pedicular screw according to the invention.
Figure 2:
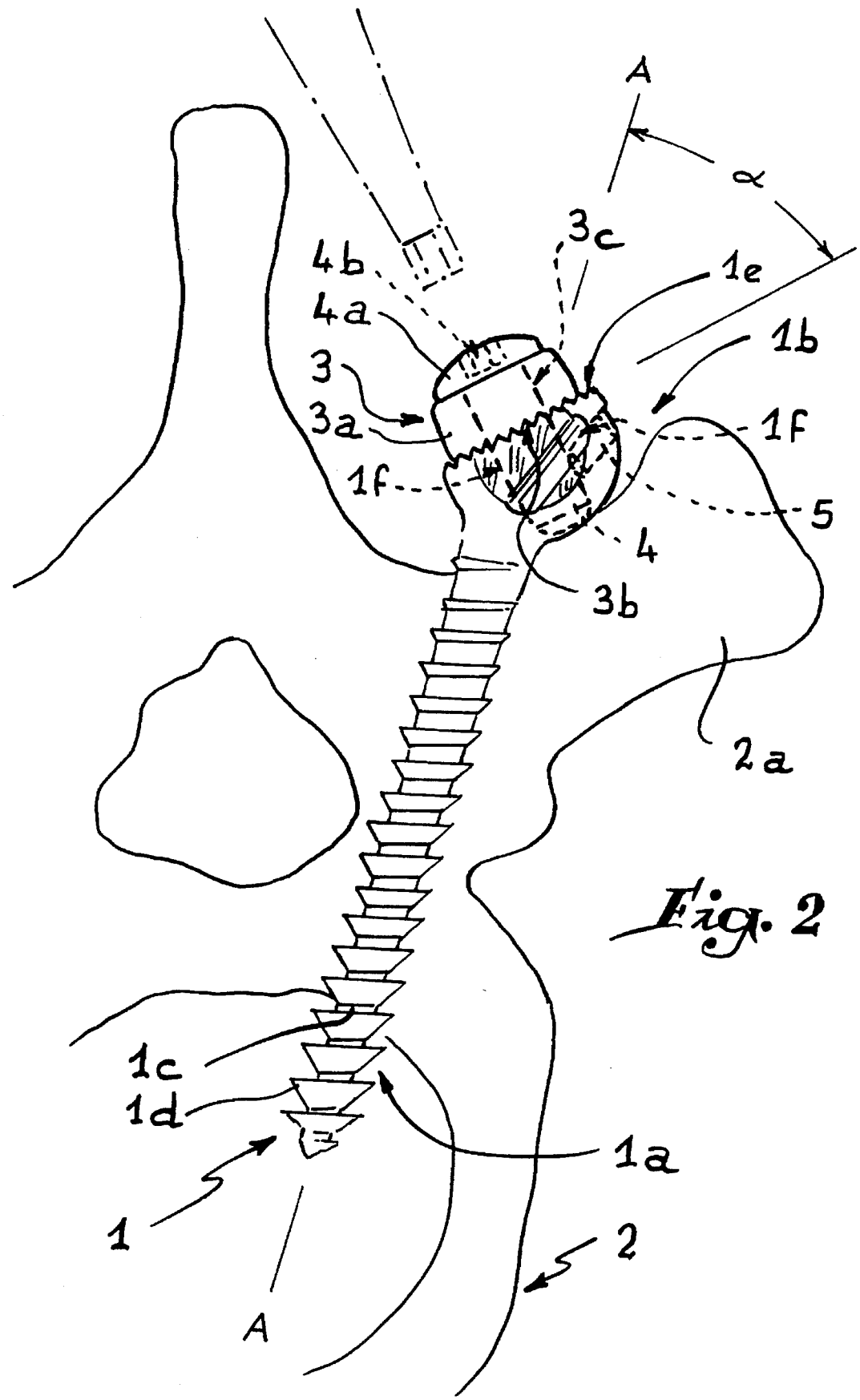
FIG. 2 is a view showing the positioning of the screw in the pedicle of a vertebra and illustrating the tightening of the connecting stem thereon.

Referring now to the drawings, FIGS. 1 and 2 show a pedicular screw 1 comprising a threaded part 1a and a semi-spherical head 1b.

The threaded part 1a has a conical core 1c which tapers inwardly away from the head and which is of equal resistance and a sharp thread 1d. Thread 1d is provided either with sharp conical profile, as shown in FIG. 2, over all or part of its length, or straight and sharp over the whole length of part 1a.

The head 1b of the pedicular screw 1 comprises a notched surface 1e which is inclined with respect to the elongated axis A—A of the screw by an angle α of about 30° to 45°.

The spherical head 1b is provided in the middle of the notched surface 1e and perpendicularly thereto, with an opening tapped hole 1f.

Another hole 1g is provided along an axis B—B parallel to the vertical axis of the pedicular screw 1, so that it communicates with the tapped hole 1f.

The pedicular screw 1 is mounted on the pedicles 2a of each vertebra 2 of a backbone (FIG. 2). The notched surface 1e is provided to receive the ends 3a of a connecting stem 3 of a lumbar-sacral fixator. Each end 3a has a surface 3b corresponding to that of the notched surface 1e of the pedicular screw 1, for the connection to be perfect.

A bolt 4 traverses the bore 3c made in each of the ends 3a of the connecting stem 3 to screw in the tapped hole 1f of the pedicular screw 1. Bolt 4 comprises a head 4a provided with a hexagonal recess 4b.

It will be noted that the inclination of the notched surface 1e which is inclined upwardly relative to the threaded part allows the operator to use a simple screwdriver to tighten the bolt 4 in the tapped hole 1f. When tightening of the connecting stem 3 on the head of the pedicular screw 1 is effected with the aid of a bolt 4, the operator introduces into hole 1g a stop or set screw 5 which immobilizes the bolt from rotation.

It will be noted that the use of a screwdriver cooperating with a bolt 4 provided with a hexagonal recess 4b which is sunk in the body of the screw, reduces the thickness of the head and thus reduces dimensions.

It will be noted that the inclination of the notched surface 1e splits the rotation about the bolt 4 into a rotation in the plane parallel to the axis of the pedicular screw and into a rotation in the direction perpendicular to the axis of the screw.

The threaded part 1a guarantees optimum resistance, while the profile of the thread 1d makes it possible solidly to anchor in the osseous part of the pedicle, thus avoiding damaging the anterior cortex of the vertebral body.

Moreover, it must be understood that the foregoing description has been given only by way of example and that it in no way limits the domain of the invention which would not be exceeded by replacing the details of execution described by any other equivalents.

What is claimed is:

1. A screw for a lumbar-sacral fixator, comprising a threaded part and a head, the screw having an elongated axis, said head having a notched surface which is inclined with respect to the elongated axis and away from the threaded part by an angle of from about 30° to 45°, and said head defining a first tapped hole which extends perpendicularly to the notched surface and a second tapped hole which communicates with the first hole.

2. The screw of claim 1, wherein the threaded part has a conical core and a sharp thread.

3. The screw of claim 1, wherein the second hole extends generally parallel to the elongated axis of the screw.

4. The screw of claim 3, further comprising a set screw received within the second hole.

5. The screw of claim 4, further comprising a bolt received within the first hole.

6. The screw of claim 1, wherein the first hole is positioned generally centrally of the notched surface.

7. The screw of claim 1, wherein said head is spherical shaped.

8. In combination:

a screw for a lumbar-sacral fixator, said screw comprising a threaded portion and a head, said screw having an elongated axis, said head having a first notched surface inclined at an angle of from about 30° to 45° with respect to the elongated axis and facing away from the threaded portion, said head defining a first tapped hole through the notched surface and a second tapped hole communicating with the first hole;

a lumbar-sacral fixator comprising a stem having opposed ends, the ends each having a second notched surface for engaging said first notched surface of said head, and an opening extending through each end; and bolt means for extending through the opening in one of the ends of said stem and into the first tapped hole to secure said stem to said screw.

9. The combination of claim 8, wherein said head of said screw is spherical shaped.

10. The combination of claim 8, wherein the second hole extends generally parallel to the elongated axis of the screw.

11. The combination of claim 8, further comprising screw means mounted within the second hole for locking the bolt means within the first hole.

* * * * *